United States Patent [19]

Pawlowski

[11] Patent Number: 4,777,142
[45] Date of Patent: Oct. 11, 1988

[54] NOVEL 1,3,4-TRI-(HET-)ARYL-ISOQUINOLINES, PROCESS FOR THEIR PREPARATION AND THEIR USE AS PHOTOCONDUCTIVE COMPOUNDS

[75] Inventor: Georg Pawlowski, Wiesbaden, Fed. Rep. of Germany

[73] Assignee: Hoechst Aktiengesellschaft, Fed. Rep. of Germany

[21] Appl. No.: 879,297

[22] Filed: Jun. 27, 1986

[30] Foreign Application Priority Data

Jun. 28, 1985 [DE] Fed. Rep. of Germany ....... 3523180

[51] Int. Cl.$^4$ ............................................. G03G 5/06
[52] U.S. Cl. ......................................... 430/78; 430/57
[58] Field of Search ............................. 430/76, 78, 57

[56] References Cited

U.S. PATENT DOCUMENTS 3,257,203 6/1966 Sues et al. ............................ 430/78
4,251,609 2/1981 Nonnemacher .................. 430/37 X

OTHER PUBLICATIONS

Chem. Ber., 71, 64 (1938) W. Krabbe et al.
J. Org. Chem., 37, 2508 (1972) V. Nair.
Heterocycles, 14, 789 (1980) Sh. Mataka et al.
A.CH. 19, 297 (1910) A. Guyot and A. Haller.

Primary Examiner—J. David Welsh
Attorney, Agent, or Firm—Schwartz Jeffery Schwaab Mack Blumenthal & Evans

[57] ABSTRACT

The invention relates to 1,3,4-tri-(het-)-aryl-isoquinoline photoconductive compounds represented by the formula:

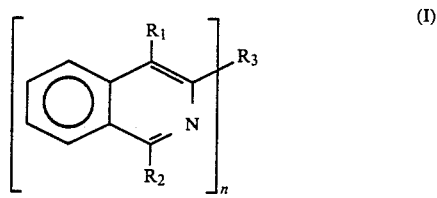

wherein $R_1$ and $R_2$ are identical or different and each denotes di($C_1$ to $C_4$)alkylaminophenyl, julolidyl or aminophenyl, with the nitrogen atom being part of a heterocyclic, 5- or 6-membered ring; $R_3$ denotes (i) a group selected from phenyl, a more highly aggregated hydrocarbon and phenylene, which group is optionally substituted by at least one halogen, nitro group, mono- or di($C_1$ to $C_4$)alkylamino group, mono- or diarylamino group, ($C_1$ to $C_4$) alkyl group or ($C_1$ to $C_4$)alkoxy group, methylene-dioxy group, amino($C_1$ to $C_4$)alkyl group or sulfonamido group, or (ii) denotes a 5- or 6-membered heterocyclic ring which contains nitrogen, oxygen or sulphur and is optionally substituted; and n denotes 1 or 2. The isoquinolines are obtained by reacting appropriate diketones with aromatic aminomethyl compounds in a basic condensation medium. The isoquinolines of formula (I) possess excellent photoconductive properties.

1 Claim, 1 Drawing Sheet

NOVEL 1,3,4-TRI-(HET-)ARYL-ISOQUINOLINES, PROCESS FOR THEIR PREPARATION AND THEIR USE AS PHOTOCONDUCTIVE COMPOUNDS

BACKGROUND OF THE INVENTION

The present invention relates to novel 1,3,4-tri-(het-)aryl-isoquinolines, to processes for the preparation of these compounds, and to their use as photoconductive compounds, for example, in the field of electrophotography or xerography.

A number of processes for the preparation of 1,3,4-triaryl-isoquinolines, in particular of 1,3,4-triphenyl-isoquinoline, have been disclosed by prior art publications. According to W. Krabbe et al, *Chem. Ber.* 71:64 (1938), for example, 1,3,4-triphenyl-isoquinoline is prepared by dehydrating benzaminotriphenyl-ethyl alcohol with phosphorus pentoxide. The compound can also be obtained by an acidic decomposition of benzoazanorcarane, as disclosed by V. Nair, *J. Org. Chem.* 37:2508 (1972). Finally, synthesis of 1,3,4-triphenylisoquinoline and a number of further derivatives has been performed by reacting 1,2-dibenzoylbenzene with appropriate aminomethyl-aromatic compounds under basic condensation conditions (Sh. Mataka et al, *Heterocycles* 14:789 (1980)).

SUMMARY OF THE INVENTION

It is an object of the present invention to provide novel isoquinoline compounds which are particularly suitable for use as highly sensitive photoconductors.

It is also an object of the present invention to provide a process for synthesizing the above-mentioned isoquinoline compounds which is relatively inexpensive and simple to carry out.

It is yet another object of the present invention to provide a recording material that includes a photoconductive layer containing a 1,3,4-tri-(het-)aryl-isoquinoline, among other constituents.

In accomplishing the foregoing objects, there has been provided, in accordance with one aspect of the present invention, a 1,3,4-tri-(het-)aryl-isoquinoline compound represented by the formula:

(I)

wherein
$R_1$ and $R_2$ are identical or different, and each denotes di($C_1$ to $C_4$)alkylaminophenyl, julolidyl or aminophenyl, with the nitrogen atom being part of a 5- or 6-membered heterocyclic ring;
$R_3$ (i) denotes a substituent selected from phenyl, more highly aggregated hydrocarbon or phenylene, which substituent is unsubstituted or substituted by at least one halogen, nitro group, mono- or di($C_1$ to $C_4$)alkylamino group, mono- or diarylamino group, ($C_1$ to $C_4$)alkyl group or ($C_1$ to $C_4$)alkoxy group, methylenedioxy group, amino($C_1$ to $C_4$)alkyl group or sulfonamido group; or (ii) denotes a 5- or 6-membered heterocyclic ring which contains nitrogen, oxygen or sulphur, and n is 1 or 2.

In a preferred embodiment, $R_3$ is a 5- or 6-membered heterocyclic ring and $R_3$ denotes furanyl, thienyl, pyridyl, julolidyl or benzimidazolyl.

In accordance with another aspect of the present invention, there has been provided a process for the preparation of a compound within formula (I) above, comprising the steps of (a) reacting a diketone compound represented by the formula:

(II)

at a temperature between 60° C. and 200° C., in a reaction mixture comprising a solvent which contains a basic condensation agent, with an aminomethyl compound represented by the formula:

(III)

wherein $R_1$, $R_2$ and $R_3$ have the meanings indicated above; and (b) separating the reaction product from the reaction mixture.

There has also been provided recording material comprised of a supported photoconductive layer which contains a 1,3,4-tri-(het-)aryl-isoquinoline as described above.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Photoconductive compounds of the present invention which are preferably employed are those conforming to formula (I) wherein:
$R_1$ and $R_2$ are identical or different, and each denotes 4-di($C_1$ to $C_4$)alkylaminophenyl;
$R_3$ (i) denotes phenyl or a more highly aggregated hydrocarbon which is unsubstituted or substituted by at least one halogen, nitro group, mono- or di($C_1$ to $C_4$)-alkylamino group, mono- or diarylamino group, ($C_1$ to $C_4$)alkyl group or ($C_1$ to Chd 4)alkoxy group, methylene-dioxy group, amino($C_1$ to $C_4$)alkyl group or sulfonamido group; or (ii) denotes a 5- or 6-membered heterocyclic ring which contains nitrogen, oxygen or sulphur, and n denotes 1.

Photoconductive compounds of the present invention which have been found to be particularly suitable as photoconductors include those conforming to formula (I) wherein:

$R_1$ and $R_2$ denotes 4-dimethyl-aminophenyl or 4-diethylaminophenyl, $R_3$ denotes phenyl or naphthyl, which are optionally substituted by at least one halogen, ($C_1$ to $C_4$)alkyl group, ($C_1$ to $C_4$)-alkoxy group, methylene-dioxy group or amino($C_1$ to $C_4$)alkyl group, and n denotes 1.

Suitable solvents for use in preparing the isoquinolines of the present invention include ethanol, ethylene glycol monomethyl ether, ethylene glycol monoethyl ether, butanol and dimethyl formamide. In accordance with the present invention, the reaction between the formula (II) diketone and the formula (III) aminomethyl compound is preferably performed in the presence of an alcoholate of an alkali metal.

For substituents $R_1$, $R_2$ and $R_3$ in the abovementioned formulas (I)–(III), the preferred number of carbon atoms contained in the alkyl or alkoxy groups, as well as in the groups derived therefrom, varies between 1 and 4.

As previously indicated, the preparation and working up of compounds within the present invention entails reacting an appropriately substituted diketone of formula (II) with an aminomethyl compound of formula (III) in a solvent containing an admixture of a strongly basic condensation agent. Suitable formula (II) diketones include compounds such as, 1,2-bis(4-dimethyl-amino-benzoyl)-benzene or 1-(4-diethyl-aminobenzoyl)-2-(4-dimethylaminobenzoyl)-benzene, which are prepared by known methods (see, e.g., A. Guyot and A. Haller, A. Che. 19:297 (1910)). Other ketones which conform to formula (II), but which have not yet been expressly described in literature, such as 1-(4-dimethyl-amino-benzoyl)-2-(4-morpholinobenzoyl)-benzene, can also be prepared employing the known methods.

But since the preparation of the diketones of formula (II) by means of these known methods is quite expensive and time-consuming, a simplified process for the preparation of desired ketones like 1,2-bis(4-diethylaminobenzoyl)-benzene is provided by the present invention. The simplified synthesis process of the present invention is described in Example 1 below.

Suitable aminomethyl derivatives within formula (III) include benzylamine, chlorobenzylamines, nitrobenzylamines, methylbenzylamines, methoxybenzylamines, dialkyl-aminobenzylamines, diarylaminobenzylamines, aminomethylbenzylamines and aminomethylpyridines, aminomethylthiophene, aminomethylfuran and aminomethylbenzimidazole. Many of these formula (III) compounds are commercially available, and all can be prepared by at least one of a number of known syntheses.

The reaction of the diketones of formula (II) with the aminomethyl derivative of formula (III) is preferably carried out in polarprotic solvents or solvent mixtures. Examples of suitable solvents are alcohols, ether alcohols and substituted formamides. Pyrrolidones and specific sulfoxides may also be used. Ethanol, ethylene glycol monomethyl ether, ethylene glycol monoethyl ether, butanol and dimethylformamide are examples of particularly preferred solvents. In general, the choice of the most appropriate solvent is determined by the requirement that the desired formula (I) reaction product be as insoluble in the solvent as possible and be able to crystallize out from the reaction mixture.

Sodium hydroxide, potassium hydroxide, sodium hydride, sodium amide and, in particular, alcoholates of alkali metals, such as sodium methylate, sodium ethylate or potassium-t-butanolate, are employed as basic condensation agents. The above-described reactants used in the present invention are preferably reacted in an alcohol in the presence of the corresponding alkali metal alcoholate.

The stoichiometry of the reactants can be varied within wide limits. To prepare the isoquinonlines of the present invention wherein n=1, the quantity of the formula (III) aminomethyl compound employed usually amounts to 1.5 to 5 times the amount of the formula (II) diketone present. To prepare the isoquinolines wherein n=2, the employed quantity of the formula (II) diketone is about twice that of the aminomethyl compound of formula (III). The stoichiometric ratio of base to formula (III) aminomethyl compound is determined by the strength of the employed base, i.e., the excess of the base may range from 1.1-fold to 10-fold.

The ratio of solvent to the sum of the reactants can also be varied within a very wide range in accordance with the instant invention. In general the weight ratio of solvent to the sum of formula (II) diketone and formula (III) aminomethyl compound ranges between 5:1 and 50:1.

The synthesis process according to the present invention can be performed within a relatively wide range of temperatures, varying between about 60° C. and 200° C., preferably between 80° C. and 140° C.

The time required for completing the reaction varies between 2 and 24 hours, depending on the selected reaction temperature and on the type of reactants and base used. Preference is given to a duration of 4 to 5 hours.

As a rule, the process of the present invention is performed such that the basic condensation agent is first added to the solvent, with the formula (II) diketone and the formula (III) aminomethyl compound added subsequently. If the formula (III) aminomethyl compounds used are sensitive to air, the reaction can be performed in an inert gas atmosphere, for example, a nitrogen atmosphere. If an otherwise suitable aminomethyl derivative of formula (III) decomposes when being exposed to the atmosphere under ambient conditions, it is also possible, in accordance with the present invention, to perform the reaction using salts of the corresponding aminomethyl compound, particularly hydrochloric or sulphuric acid salts.

The mixture is heated to the desired temperature with stirring, whereby usually clear solutions of gradually deepening color are obtained. In some cases crystallization of isoquinolines within the present invention starts during the reaction period; in those cases where the solution remains clear, it is cooled down until a general crystallization of the reaction products takes place. The reaction products are then separated from the reaction mixture, dried and, if appropriate, recrystallized. Solvents or solvent mixtures of lower polarity, such as toluene or toluene/hexane, have been found to be particularly suitable for the recrystallization process.

If no (or only incomplete) crystallization of the formula (I) compounds of the present invention takes place, they can be precipitated from the reaction mixture by the addition of a nonsolvent, isolated by filtration and purified by crystallization. Alternatively, they can be isolated by extraction.

In general, this process in accordance with the present invention results in high product yields.

In most cases, the novel 1,3,4-tri-(het-)-arylisoquinolines of formula (I) are stable solids of faint to strong yellow color, which upon irradiation with UV-light exhibit very strong blue fluorescent shades. Moreover, they all possess good to excellent photoconductor properties. Since they have a relatively low tendency to crystallize in mixtures with polymeric binders, they are particularly suitable for use as photoconductive compounds in the preparation of photoconductive layers in electrophotography and xerography, for example, in the fields of planographic printing and resist technology.

The present invention will now be explained in greater detail by way of the following, nonlimiting exemplary embodiments. Percentages always denote percent by weight, and melt and boiling points are uncorrected, unless otherwise indicated.

As noted above, the known syntheses of starting compounds conforming to formula (II) are usually rather expensive and time-consuming; an alternative way of preparing numerous formula (II) diketones will therefore be described first.

EXAMPLE 1

Preparation of 1,2-bis(4-diethylaminobenzoyl)benzene 335 g (2.5 moles) of aluminum chloride were added to 1,000 ml of dry carbon disulfide with vigorous stirring, and the mixture was cooled to about 10° C. Through a dropping funnel, 560 g (3.75 moles) of diethylaniline were dropwise added within about 30 minutes, while the temperature of the mixture was kept below 15° C. by cooling with ice. The dropping funnel was then rinsed with 50 ml of carbon disulfide. The resulting mixture, which had an intensive green color, was cooled to 0° C., and a solution of 132 g (0.65 mole) of phthalic acid dichloride in 200 ml of carbon disulfide was added through the dropping funnel, the temperature being kept constant. When the addition was completed, the mixture was slowly heated to room temperature and then heated to reflux for 1 hour.

The mixture was allowed to cool down and then was carefully mixed with about 300 ml of nitromethane. It was thereafter cooled to 0° C. The resulting ketone/aluminum complex, which was by then dissolved, was carefully decomposed by slowly adding 500 g of ice. After complete decomposition, the solvents and the excess diethylaniline were removed by water vapor distillation, whereby the ketone crystallized from the aqueous solution. Complete crystallization was achieved overnight, and then the product was removed by suction, washed in aqueous ethanol and dried. The product was thereafter dissolved in methylene chloride and filtered using neutral aluminum oxide. The resulting solution of intensive yellow color was concentrated, and the product was recrystallized from ethanol.

Yield: 203 g (72% of theory) of faint yellowish crystals.

Elemental analysis $C_{28}H_{32}N_2O_2$: Calc: C: 78.4%, H: 7.5%, N: 6.5%, Found: C: 78.6%, H: 7.8%, N: 6.6%.

Melting point: 172.5° to 173.5° C.

UV (MeOH): 248, 363 nm.

EXAMPLE 2

Preparation of 1,4-bis(4-dimethyl-aminophenyl)-3-phenyl-isoquinoline 3.4 g (148 mmoles) of sodium were dissolved, with stirring, in 200 ml of ethylene glycol monomethyl ether. 12.5 g (33 mmoles) of 1,2-bis(4-dimethylaminobenzoyl)-benzene and 14.4 g (135 mmoles) of benzylamine were added to the clear solution, and the mixture was heated to reflux. After about 3 hours a yellow powder started to crystallize out. The mixture was heated for another 2 hours, cooled down and allowed to stand for some time until crystallization was completed. The crystallized product was filtered off, washed with aqueous ethanol, and dried. The raw product thus obtained had a melting range from 245° to 249° C. It was purified by recrystallization from toluene/ethanol.

Yield: 12.7 g (85% of theory) of faint yellowish crystals fluorescing in strong blue shades.

Elemental analysis $C_{31}H_{29}N_3$: Calc: C: 83.9%, H: 6.6%, N: 9.4%. Found: C: 84.0%, H: 6.8%, N: 9.4%.

Melting point: 251° to 253° C.

UV (MeOH): 281, 375 nm.

EXAMPLE 3

Preparation of 1,4-bis(4-diethylaminophenyl)-3-(4-aminomethyl-phenyl)-isoquinoline 1.15 g (50 mmoles) of sodium were dissolved in 60 ml of ethylene glycol monomethyl ether. 4.29 g (10 mmoles) of the diketone described in Example 1 and 5.45 g (40 mmoles) of 4-aminomethylbenzylamine were added and the mixture was heated to reflux for 5 hours. After a certain time, crystallization of a small quantity of a yellow compound was observed. As no further crystallization takes place after the mixture was cooled, the crystallized yellow powder was filtered off. It was present in an amount of 0.4 g and was identified as the dimeric isoquinoline (see Example 4). The yellow filtrate was mixed with water, and the resulting oily product was isolated by decanting the solution.

Digestion in ethanol gave a semi-crystalline product. The raw yield was 4.1 g (77% of the theoretical yield). The product was recrystallized from methanol, providing yellow crystals.

Elemental analysis $C_{36}H_{40}N_4$: Calc: C: 81.8%, H: 7.6%, N: 10.6%. Found: C: 81.9%, H: 7.7%, N: 10.4%.

Melting point: 142° to 143° C.

UV (MeOH): 276, 375 nm.

EXAMPLE 4

Preparation of 1,4-bis(3-(1,1',4,4'-tetrakis-(4-diethylaminophenyl))-isoquinolinyl)-benzene 2.3 g (100 mmoles) of sodium were dissolved in 100 ml of ethylene glycol monomethyl ether. 7.5 g (18 mmoles) of the diketone described in Example 1 and 1.2 g (9 mmoles) of 4-aminomethyl-benzylamine were added, and the mixture was heated to reflux for 16 hours. After cooling down, the precipitated yellow product was filtered off and recrystallized from toluene.

Yield: 4.3 g (46% of theory) of yellow crystals.

Elemental analysis $(C_{64}H_{68}N_6)$: Calc: C: 83.4%, H: 7.4%, N: 9.1%. Found: C: 83.3%, H: 7.7%, N: 9.1%.

Melting point: 226° to 267° C.

UV (MeOH): 275, 367 nm.

EXAMPLES 5 TO 37

The compounds listed below were prepared via the reaction described in Example 2, except that in each case the duration of the reaction, the ratio of reactants to solvent and the working-up conditions were slightly modified. The examples marked with an asterisk (*) were performed in accordance with Example 4. The examples marked with two asterisks (**) yielded isomeric product mixtures which were not further split up.

| Example No. | $R_1$ | $R_2$ | $R_3$ | Melting Point (°C.) (recrystallization solvent) |
|---|---|---|---|---|
| 5 [1] | –C₆H₄–N(CH₃)₂ | –C₆H₄–N(CH₃)₂ | –C₆H₄–CH₃ | 220–222° C. (Toluene/hexane) |
| 6 [1] | –C₆H₄–N(CH₃)₂ | –C₆H₄–N(CH₃)₂ | –C₆H₄–OCH₃ (ortho) | 194–195° C. (Dimethyl formamide (DMF)/H₂O) |
| 7 [1] | –C₆H₄–N(CH₃)₂ | –C₆H₄–N(CH₃)₂ | –C₆H₄–F | 230–231.5° C. (Toluene/n-hexane) |
| 8 [1] | –C₆H₄–N(CH₃)₂ | –C₆H₄–N(CH₃)₂ | pyridyl | 236–239° C. (Toluene/n-hexane) |
| 9 [1] | –C₆H₄–N(CH₃)₂ | –C₆H₄–N(CH₃)₂ | benzimidazolyl (NH) | 346–347° C. (DMF) |
| 10** [1] | –C₆H₄–N(CH₃)₂ | –C₆H₄–N(C₂H₅)₂ | –C₆H₅ | 192–213° C. (Toluene/n-hexane) |
| 11 [1] | –C₆H₄–N(C₂H₅)₂ | –C₆H₄–N(C₂H₅)₂ | –C₆H₅ | 142–143° C. (Ethanol) |
| 12 [1] | –C₆H₄–N(C₂H₅)₂ | –C₆H₄–N(C₂H₅)₂ | –C₆H₄–CH₃ | 158° C. (Toluene/n-hexane) |
| 13 [1] | –C₆H₄–N(C₂H₅)₂ | –C₆H₄–N(C₂H₅)₂ | –C₆H₄–OCH₃ (ortho) | 151.5–152.5° C. (Toluene/n-hexane) |
| 14 [1] | –C₆H₄–N(C₂H₅)₂ | –C₆H₄–N(C₂H₅)₂ | –C₆H₄–OCH₃ (meta) | 141.5–143° C. (Toluene/n-hexane) |
| 15 [1] | –C₆H₄–N(C₂H₅)₂ | –C₆H₄–N(C₂H₅)₂ | –C₆H₄–OCH₃ (para) | 195–196.5° C. (Toluene/n-hexane) |

-continued

| Example No. | R₁ | R₂ | R₃ | Melting Point (°C.) (recrystallization solvent) |
|---|---|---|---|---|
| 16 [1] |  |  |  | 179–180.5° C. (Toluene/n-hexane) |
| 17 [1] |  |  |  | 144–145° C. (Toluene/n-hexane) |
| 18 [1] |  |  |  | 138–138.5° C. (n-hexane) |
| 19* [2] |  |  |  | 216–217° C. (Toluene/n-hexane) |
| 20 [1] |  |  |  | 145–146° C. (Toluene/n-hexane) |
| 21 [1] |  |  |  | 166–167° C. (Toluene/n-hexane) |
| 22 [1] |  |  |  | 149–150° C. (Toluene/n-hexane) |
| 23 [1] |  |  |  | 194–195° C. (Toluene/n-hexane) |
| 24 [1] |  |  |  | 167–169° C. (Toluene/n-hexane) |
| 25 [1] |  |  |  | 148–149° C. (Toluene/n-hexane) |
| 26 [1] |  |  |  | 162–164° C. (Toluene/n-hexane) |

-continued

| Example No. | | R₁ | R₂ | R₃ | Melting Point (°C.) (recrystallization solvent) |
|---|---|---|---|---|---|
| 27 | 2 |  |  |  | 188.5–189° C. (DMF) |
| 28 | 1 |  |  |  | 209–210° C. (Toluene) |
| 29 | 1 |  |  |  | 226–228° C. (Methanol/H₂O) |
| 30 | 1 |  |  |  | 163–164.5° C. (Toluene/n-hexane) |
| 31 | 1 |  |  |  | 223.5–225° C. (Toluene/n-hexane) |
| 32 | 1 |  |  |  | 205–206.5° C. (Toluene/n-hexane) |
| 33 | 1 |  |  |  | 218–218.5° C. (Toluene/n-hexane) |
| 34 | 1 |  |  |  | 191–192.5° C. (Toluene/n-hexane) |
| 35 | 2 |  |  |  | 157–158° C. (Toluene/n-hexane) |
| 36 | 1 |  |  |  | 207° C. (DMF/H₂O) |
| 37** | 1 |  |  |  | 167–183° C. (Toluene/n-hexane) |

EXAMPLE 38

A diketone having the formula indicated below was prepared as described in Example 1 by reacting julolidine with phthalic acid dichloride. The resulting product had the following structure and, upon being heated, decomposed without having a defined melting point, whence it assumed a dark shade.

Elemental analysis ($C_{32}H_{32}N_2O_2$): Calc: C: 80.6%, H: 6.8%, N: 5.9%. Found: C: 80.4%, H: 6.9%, N: 5.9%.

10 mmoles of the compound thus obtained were dissolved in a solution of 50 ml of ethylene glycol monomethyl ether and 50 mmoles of sodium. Dry nitrogen was bubbled through the mixture to exclude air and moisture, then 40 mmoles of benzylamine were added to the mixture, which was then heated to reflux. After 4 hours, the mixture was allowed to cool; the resulting product which precipitated after some time was filtered off and washed with ethanol. 4.87 g of a yellow powder were obtained, corresponding to 89% of the theoretical yield, which took on a reddish color when it was exposed to the air over a prolonged time, eventually displaying a dark color and signs of decomposition. The powder did not melt when it was heated to 350° C. in order to determine its melting point. Chromatographic recordings (toluene/butyl acetate, 3:1; silica gel) showed a uniform compound of intensive, fluorescent green-bluish color, which compound corresponded to the following formula Elemental analysis ($C_{39}H_{37}N_3$): Calc: C: 85.5%, H: 6.8%, N: 7.7%. Found: C: 85.7%, H: 6.5%, N: 7.8%.

While numerous electrophotographic processes, materials and variants for the use of recording materials are known, the increasing stringent standards which these reproduction systems must satisfy create a demand for new, highly sensitive photoconductors. The isoquinoline derivatives synthesized, in accordance with the present invention, in Examples 2 to 38 exhibit excellent properties when used as photoconductive compounds ("charge transporting compounds"), so that they can be employed to great advantage in highly sensitive electrophotographic recording materials, for example, printed circuits and planographic printing forms. The compounds of the present invention are also suitable for materials used in cyclically working processes, for example, in copying machines.

The photoconductive compounds according to this invention are used to advantage in both single-layer and multilayer recording materials, as shown diagrammatically in FIGS. 1 through 5. Component 1 in each drawing is an electrically conductive layer support, component 2 is a charge carrier-generating layer, and component 3 is a charge transporting layer containing photoconductor (charge transporting) compounds with the present invention. Component 4 is an insulating intermediate layer. Component 5 is a layer comprised of a charge carrier generating material dispersed in a binder. Component 6 denotes a photoconductive layer comprised of a photoconductive compound according to the present invention, a charge-generating compound which may be present in a homogeneous or disperse form, a binder, etc.

Figure 1:
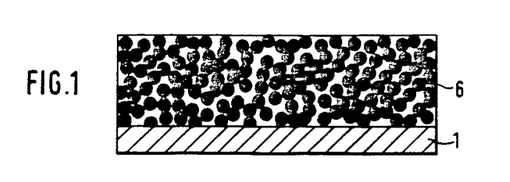
FIGS. 1–5 are schematic drawings depicting in cross-section different configurations for recording material comprising a photoconductive compound within the present invention.
Figure 2:
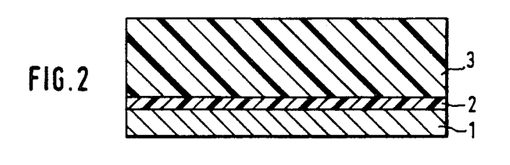

If electrophotographic recording materials are used for planographic printing plates, preference is given to single-layer systems where the layer is comprised of binder, photoconductor and charge carrier-generating compound (FIG. 1). In general, a solution or dispersion of the components in an organic solvent is applied to the layer support such that a dry layer having a thickness of 0.5 to 40 μm is obtained. Preferably, the layers have a thickness of 2 to 15 μm.

Figure 3:
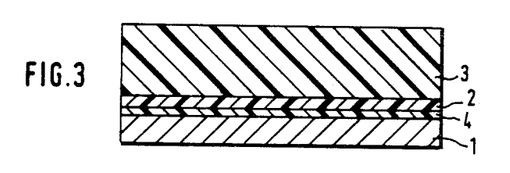
Figure 4:
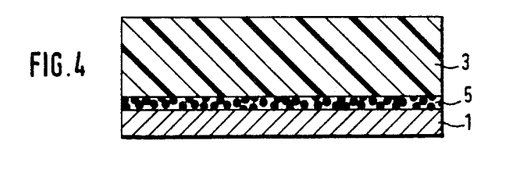
Figure 5:
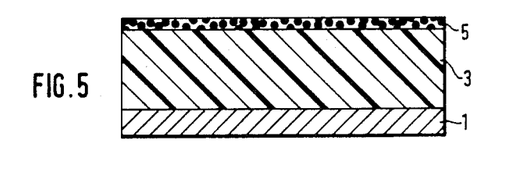

If the recording material is employed for copying purposes, multilayer arrangements are favorable (FIGS. 2 to 5). The charge carrier-generating layer 2 or 5 has a preferred thickness of less than 0.8 μm, and the layer 3 containing the photoconductor in general has a thickness of between 2 and 30 μm. The electrophotographic properties of recording material within the present invention can be further improved by introducing an insulating intermediate layer 4, which acts as a barrier layer or an adhesion-promoting layer (FIG. 3). Its thickness depends on the intended use and can be varied between 10 nm and 2 μm.

The materials which may be used as conductive layer supports include all electrically conductive materials that can be provided with a continuous planar surface coating. Layer supports consisting of 80 to 500 μm thick aluminum, zinc, magnesium or copper sheets, or so-called multimetal plates, are suitable, for example, for use as planographic printing plates. If desired, these support materials can be pretreated, grained and anodically oxidized by suitable methods, in accordance with their intended application. Apart from aluminum sheets and foils, other preferred layer support materials include plastic films having a metallized or vapor-deposited surface, such as polyethylene or polyester having a vapor-deposited aluminum coating or electrically conductive special-purpose paper.

In the field of xerography, layer supports of this type are also employed in the form of drums or endless belts.

Although some of the photoconductors according to this invention possess film-forming properties, it is usually expedient to add a polymeric binder in order to improve their layer properties. The binders are selected in accordance with the intended application. In the copying field, suitable binders in particular include cellulose esters, polyesters, polyvinyl chlorides, polyvinyl acetates, polycarbonates, acrylic and methacrylic resins, and copolymers such as styrene/maleic acid anhydride copolymers, vinyl chloride/maleic acid anhydride copolymers and styrene/butadiene copolymers. These binders are suitable both for the charge-transporting and the charge-generating layers, and are especially preferred because of their film-forming, adhesive and electrical properties.

Binders which are soluble in acid or, preferably, alkaline, aqueous-alcoholic or aqueous solvent mixtures are particularly suited for planographic printing plates and printed circuits. Apart from good solubility, film-forming and adhesive properties, long print runs and physiological safety are decisive advantages for binders which are suitable in this context.

High molecular weight binders possessing satisfactory solubility in alkaline media are advantageously employed. Alkali-solubility is achieved by incorporating specific groups, for example, acid anhydride groups, carboxyl groups, phenolic and aliphatic hydroxyl group, sulfonic acid groups, sulfonamide groups and sulfonimide groups, and by incorporating urethane groups activated by electron-attracting groups.

Copolymers containing acid anhydride groups, carboxyl groups, partly esterified acid anhydride groups, and phenolic resins are particularly suitable for the manufacture of photosensitive layers for the printing industry. More specifically, compositions of this type combine excellent electrophotographic properties and very good printing properties. Examples of particularly preferred polymers include copolymers of styrene or substituted styrenes and maleic acid anhydride; copolymers of styrene or substituted styrene and partly esterified maleic acid anhydride; copolymers of acrylic acid, methacrylic acid and acrylic acid esters; and reaction products of polyvinyl acetals containing free hydroxy groups and sufonyl isocyanates.

If phenolic resins are used as binders, preference is given to homopolymers and copolymers of hydroxystyrene or novolak resins. The latter copolymers are obtained, for example, by condensing phenol or cresol with formaldehyde.

The layers obtained in these cases are sufficiently soluble in developers that are, for example, comprised of 70% of water, 25% of propanol and 5% of sodium metasilicate, and at the same time they exhibit good electrophotographic properties.

The resins enumerated above may be used alone or in admixture with other resins. The binders which can be employed in accordance with this invention are not restricted to the resins explicitly mentioned herein.

Although the compounds of the present invention are photoconductive, i.e., they can act in charge-generating and charge-transporting, the sensitivity, particularly to visible light, of an electrophotographic recording material containing these compounds can be considerably increased, especially in spectral ranges of special interest, by the addition of sensitizing dyestuffs or pigments. The following substances can be employed in single-layer systems: dyestuffs of the triarylmethane series and/or xanthene dyestuffs, oxazine dyestuffs, thiazine dyestuffs, cyanine dyestuffs, pyrylium dyestuffs, quinacridone dyestuffs or indigo-type dyestuffs, such as Rhodamine FB (C.I. 45,160), Malachite Green (C.I. 42,000), Methyl Violet (C.I. 42,535), Crystal Violet (C.I. 42,555). Brilliant Green (C.I. 42,040), Methylene Blue (C.I. 52,015), Methylene Green (C.I. 52,020), Capryl Blue (C.I. 48,035), Astrazon Yellow (C.I. 48,035), Astrazon Orange (C.I. 48,040), Astrazon Red (C.I. 48,020), Aizen Astra Phloxin (C.I. 48,070) and mixtures thereof; and inorganic or organic pigments such as zinc oxide, zinc sulfide, phthalocyanine pigments, azo pigments, perylene pigments, benzimidazole pigments and Indanthrone pigments, including the various crystal forms of copper phthalocyanine, N,N-dialkylperylene-tetracarboxylic acid diimides and Chlordiane Blue.

Together with the photoconductive compound, binder and, optionally, further additives, the charge carrier-generating substances are dispersed or dissolved in an organic solvent, are applied by means of known methods, for example, by blade spreading, to the layer support, and are then dried.

In multilayer systems, selenium, its alloys and charge-transferring complexes and eutectic complexes can, for example, be employed in addition to the above-listed dyes and pigments. In these cases, too, the charge carrier-generating substance is frequently dissolved or dispersed in an organic solvent, together with a binder and other additives, and applied by means of a blade; coating of the layer support is also possible, however, by sublimation or similar vapor-deposition techniques.

Further additives which may be contained in the individual layers include plasticizers, levelling agents and adhesion promoters.

The photoconductive compounds according to the present invention can be employed in combination with other, known photoconductors. Their mixing ratio with the binder can be varied within wide limits according to the application requirements, but with certain limits imposed, by the demand for maximum photosensitivity. A mixing ratio of about 1:1 parts by weight has been found to be expedient, but ratios between 4:1 and 1:2 can also be used to advantage.

In accordance with the present invention, the charge carrier-generating substance is preferably employed in an amount between about 0.01 and 30%, relative to the weight of the photoconductive compound. Quantities of 0.5 to 15% have proved particularly advantageous. If pigments are used, the concentration of charge carrier-generating substance can be even higher without adversely affecting the electrophotographic properties of the recording material of the present invention.

It is known that homogeneous layers or monodispersion layers, as illustrated in FIG. 1, generally exhibit the lowest photosensitivities. But compared with multilayers, they have the advantage of being both negatively and positively chargeable; in contrast, multilayer arrangements according to FIGS. 2, 3 and 4 can only be charged negatively, while the inverse arrangement, according to FIG. 5, permits only positive charging of these layers.

The photoconductivity of the isoquinolines according to the present invention is independent of the layer arrangement selected; they are generally suitable for all arrangements shown in FIGS. 1 through 5.

EXAMPLE 39

A coating solution containing:
30.0 g of a styrene/maleic acid anhydride copolymer having a mean molecular weight of about 80,000,
20.0 g of compound No. 11
0.1 g of Rhodamine FB (C.I. 45,170) and
0.6 g of Astrazon Orange R (C.I. 48,040), in
220.0 g of tetrahydrofuran,
140.0 g of ethylene glycol monomethyl ether and
44.0 g of butyl acetate
was blade-coated onto a 0.3 mm thick aluminum foil which had been electrochemically grained and post-treated with polyvinylphosphonic acid, such that after the evaporation of the solvent mixture a photoconductive layer having a weight of 5.8 g/m$^2$ was obtained.

The layer was charged to −450 V by means of a corona and exposed for 15 seconds in a reprographic camera using 10 halogen lamps of 600 W each. The original was a mounting flat containing the usual test elements. The latent charge image produced by the exposure was developed with a commercially available dry developer and thermally fixed; a clean, scum-free, crisp image of the original was thereby obtained.

The aluminum foil carrying the photoconductor layer with the fixed toner image was converted into a printing form by immersion in a trough which contained a decoating solution of 50 g of sodium silicate, 250 g of glycerol (80% strength), 390 g of ethylene glycol and 310 g of methanol. The decoated printing plate was rinsed with water and wiped with a blade. In the decoated areas, the layer support material was laid bare, with no noticeable staining due to color residues.

When mounted in an offset press, the printing form thus obtained gave several ten thousands of prints having good quality.

EXAMPLE 40

A recording material prepared as described in Example 39 was measured in a Dyntest apparatus. The filament lamp employed in the apparatus had a temperature of 2,800° K. The layer was charged to −500 V and the discharge in the dark was recorded. After 1 minute, the residual potential $U_D$ was −428 V, representing 85.5% of the initial charge. When the layer was charged to −500 V and then exposed, the residual potential $U_H$ measured after 1 minute was −9 V, or 1.8% of the initial charge. After 12.8 seconds, the layer is discharged to $E_{1/10}$ (−50 V), the half-value sensitivity $E_{\frac{1}{2}}$ being 12.2 μJ/cm².

EXAMPLES 41 TO 44

Coating solutions were prepared as described in Example 39, with the exception that instead of compound No. 11, compounds Nos. 12, 16, 20 and 30, respectively, were employed. The tests as in Example 40 gave the following results:

| Compound | $U_D$ (V) | $U_H$ (V) | $E_{\frac{1}{2}}$ (μJ/cm²) |
| --- | --- | --- | --- |
| 12 | −427 (85.4%) | −8 (1.6%) | 11.0 |
| 16 | −385 (77.0%) | −10 (2.0%) | 11.3 |
| 20 | −437 (87.4%) | −16 (3.2%) | 12.5 |
| 30 | −414 (82.8%) | −6 (1.2%) | 10.3 |

The recording materials prepared in Examples 41 to 44 were imaged, developed and decoated in a commercially available apparatus; they all gave good-quality printing forms which were distinguished by ready processability, high density in the solid areas, good crispness and absence of scum.

EXAMPLE 45

A coating solution was prepared as described in Example 39, except that the compound 2,5-bis-(4-diethylaminophenyl)-oxadiazole-1,3,4 (see German Pat. No. 10 58 875, equivalent to U.S. Pat. No. 3,189,447) was employed instead of compound No. 11. The following results were measured:

$U_D$(V) = −382 V (76.4%); $U_H$(V) = −11 V (2.2%); $E_{\frac{1}{2}}$ = 13.6 μJ/cm².

It has been noted above that the photoconductors of the present invention exhibit sensitivities corresponding to the sensitivity of the oxadiazole derivative that is frequently used for commercial applications. However, their discharge in the dark generally is inferior to that of the oxadiazole derivative.

EXAMPLE 46

A polyester film, which had been vapor-coated with aluminum was coated with N,N'-dimethylperylene-3,4,9,10-tetracarboxylic acid diimide, having spectral light absorption values from 430 to 600 nm, by vapor-coating in a vacuum deposition apparatus at a pressure of about $10^{-8}$ bar and a temperature of about 280° C. The homogeneously vaporized layer has a weight of about 150 mg/m² and covers the polyester support completely.

A solution comprised of equal parts by weight of compound No. 11 and a polycarbonate resin (Makrolon ®2045, made by Bayer) in tetrahydrofuran was spin-coated onto the vapor-deposited layer. The layer was dried, and its photosensitivity was determined as described above:

$U_D$(V) = −443 V (88.5%); $U_H$(V) = practically zero $E_{\frac{1}{2}}$ (μJ/cm²) = 1.65.

EXAMPLES 47 AND 48

Example 46 was repeated, except that compound No. 11 of the present invention was replaced by the comparative compounds 2-phenyl-4(2'-chlorophenyl)-5-(4'-diethyl-aminophenyl)oxazole-1,3 (German Pat. No. 11 20 875, equivalent to U.S. Pat. No. 3,257,203) and 2,5-bis-(4-diethyl-aminophenyl)-oxadiazole-1,3,4. With equal layer thicknesses, the $E_{\frac{1}{2}}$ values of the layers obtained using these comparative compounds were 2.56 μJ/cm² and 1.76 μJ/cm², respectively.

What is claimed is:

1. Recording material comprising a supported photoconductive layer which contains a 1,3,4-tri(het-)-arylisoquinoline represented by the formula wherein
R₁ and R₂ are identical or different, and each denotes di(C₁ to C₄)alkylaminophenyl, julolidyl or aminophenyl, with the nitrogen atom being part of a 5- or 6-membered heterocyclic ring;
R₃ (i) denotes a substituent selected from phenyl, a more highly aggregated hydrocarbon or phenylene, which substituent is unsubstituted or substituted by at least one halogen, nitro group, mono- or di(C₁ to C₄)alkylamino group, mono- or diarylamino group, (C₁ to C₄)alkyl group or (C₁ to C₄)alkoxy group, methylenedioxy group, amino(C₁ to C₄)alkyl group or sulfonamido group; or
(ii) denotes a 5- or 6-membered heterocyclic ring which contains nitrogen, oxygen or sulphur, and n is 1 or 2.

* * * * *